United States Patent [19]

Grussmark

[11] Patent Number: 4,827,951
[45] Date of Patent: May 9, 1989

[54] DENTAL FLOSS AND TOOTHPASTE CONTAINER

[76] Inventor: Stephen M. Grussmark, 2901 S. Bayshore Dr., Apt. 15C, Coconut Grove, Fla. 33133

[21] Appl. No.: 36,357

[22] Filed: Apr. 9, 1987

[51] Int. Cl.⁴ ............................................. A45D 40/00
[52] U.S. Cl. ...................................... 132/314; 132/324
[58] Field of Search .................. 132/93, 89, 91, 92 A, 132/92 R, 79 E

[56] References Cited

U.S. PATENT DOCUMENTS

| | | | |
|---|---|---|---|
| 811,370 | 1/1906 | Brush | 132/79 E |
| 1,050,560 | 1/1913 | Moore | 132/79 E |
| 1,439,076 | 12/1922 | Edwards | 132/79 E |
| 1,466,982 | 9/1923 | Bailey | 132/92 R |
| 1,492,836 | 5/1924 | Decker | 132/92 R |
| 1,858,134 | 5/1932 | Booth et al. | 132/79 E |
| 3,863,655 | 2/1975 | Smith | 132/91 |
| 4,231,381 | 11/1980 | Battista | 132/89 |
| 4,428,389 | 1/1984 | Sanchez Cordero | 132/79 E |
| 4,673,106 | 6/1987 | Fishman | 132/79 E |

*Primary Examiner*—John J. Wilson
*Attorney, Agent, or Firm*—John C. Malloy

[57] ABSTRACT

The device is composed of a dental container having a portion with a dispenser for discharge of a charge of toothpaste and second portion sized to receive a spool of dental floss to be removed through a hole in the container so that a length of the floss can be severed using a cutter on the container.

1 Claim, 1 Drawing Sheet

DENTAL FLOSS AND TOOTHPASTE CONTAINER

BACKGROUND OF THE INVENTION

The present invention relates to a device for use in cleaning teeth; it is composed of a container having two portions one containing a charge of toothpaste and the other housing a spool of dental floss, the housing containing the dental floss supporting the same. The container is provided with an opening through which the dental floss may be threaded to withdraw a length therefrom; and it also includes cutter means so that a length of the floss may be severed from the container.

It is known that flossing of teeth is recommended by dentists. Commonly, dentists recommend flossing during the teeth cleaning process. The present invention is of an improved container which includes a portion with a dispensing means to receive a charge of toothpaste and a portion sized to receive a spool of floss so that the two can be used as required in the teeth cleaning process. There is provided in general a compact, easily transportable device for convenient use in the teeth cleaning process.

OBJECTS OF THE INVENTION

It is an object of the present invention to provide a toothpaste and dental floss container wherein, in the preferred embodiment, the container includes a dental floss containing portion and a toothpaste containing portion, the latter being of the type including a pump-type dispenser with an exit orifice and an operator adjacent the orifice which operator is manipulated in use to operate the dispensing means.

It is another object of the present invention to provide a compact floss and pump-type toothpaste dispensing unit for use in the teeth cleaning process.

It is a further object of the present invention to provide a dental product which reminds the user to floss as well as brush his teeth for efficient cleaning of teeth.

It is also an object of the present invention to provide in combination a floss dispenser and pump-type toothpaste dispenser wherein the combination is provided with an opening to withdraw floss of a selected length and cutter means to sever the length from the combination.

SUMMARY OF THE INVENTION

Generally, the device is composed of a dental container for use in the teeth cleaning process which has a first portion with a dispensing means for discharging a charge of toothpaste and a second portion sized to receive a spool of dental floss so that a length may be removed through a hole in the container and the length of the floss can be severed using a cutter means on the container.

In one embodiment, the floss carrying device is removably mounted to the top of a pump-type toothpaste dispenser adjacent the pump operator and discharge orifice. In the embodiment shown, the toothpaste container portion includes a peripheral wall which extends upward from a top surface thereby defining a seat at the top of the toothpaste portion of the container, while the floss carrying portion includes a base sized to mate with and be receivable in the seat in snug relation. To this end, a base that is coextensive with that insertable portion may be provided which has a plurality of said walls extending upward from the lowermost base surface and a roof that forms, in combination with the side walls, a housing within which a spool of dental floss is housed. In this type embodiment, one of the side walls includes an opening through which the dental floss is threaded and extends to the distal end. On an adjacent side wall, a cutter means is provided composed of a cutting plate on the outside surface of the housing. The cutting plate has a cutting surface which, when a portion of dental floss is withdrawn from the housing, can be used to cut the floss thereby separating that portion from the remainder of the floss in the housing.

DETAILED DESCRIPTION OF A PREFERRED EMBODIMENT OF THE INVENTION

Further objects and advantages of the present invention can be found in the detailed discussion of the preferred embodiments of the invention when taken in conjunction with the accompanying drawings in which.

DETAILED DESCRIPTION OF THE PREFERRED EMBODIMENT

The present invention relates to a dental floss carrier and particularly relates to a carrier which can be mounted atop a pump-type toothpaste dispenser.

Figure 1:
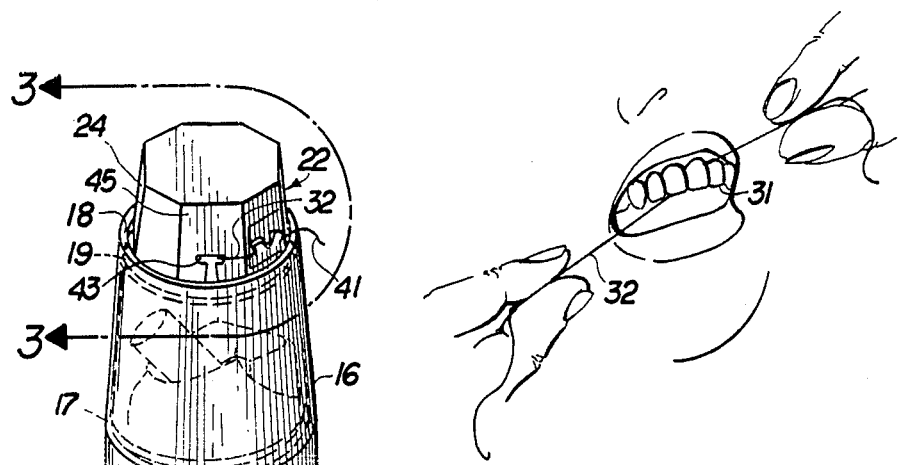
FIG. 1 illustrates the use of a portion of dental floss.

FIG. 1 illustrates dental floss portion 32 being utilized to clean tooth 31.

Figure 2:
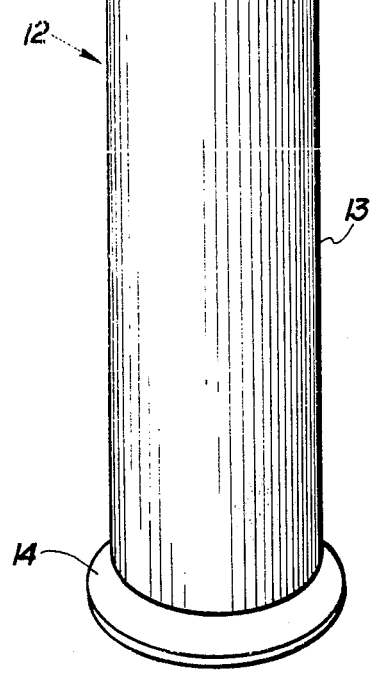
FIG. 2 illustrates a perspective view of a pump-type toothpaste dispenser with a floss carrying device mounted atop the dispenser in accordance with the principles of the present invention; and, FIG. 3 illustrates a perspective view of the floss carrying device as viewed from section lines 3'—3" in FIG. 2.

FIG. 2 is a perspective view of a container including a pump-type toothpaste portion and dispenser 12 and a dental floss housing portion 22 mounted atop the toothpaste portion 12. The dispenser 12 or toothpaste portion includes an elongated body 13 and footed base 14. A cap 16 which may be threadably attached as by threads 15 is shown in dashed lines in FIG. 2. Cap 16 encloses a pump-type dispensing mechanism 17.

Figure 3:
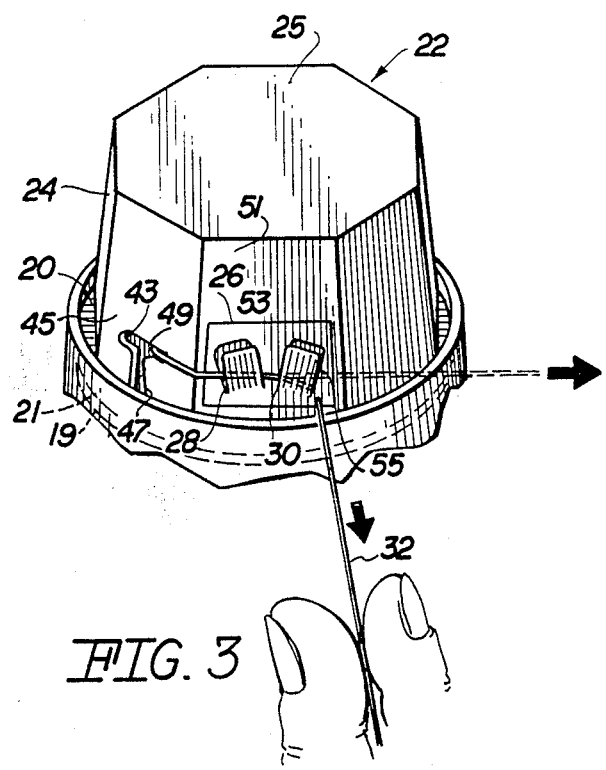

In this preferred embodiment, at the upper end of cap 16, a peripheral wall 18 extends above a top surface 19 that is shown by dashed lines in both FIGS. 2 and 3, which defines a recess or seat. Similar numbers designate similar items throughout the figures.

In one embodiment, a dental floss carrier 22 is mounted in the seat atop cap 16. To this end it is provided with an insertable portion that is defined in part by surface 20 shown in FIG. 3. Surface 20 has peripheral edge 21 that has a complementary shape and size to that of the seat defined by peripheral walls 18 and top surface 19 of cap 16.

In another embodiment, the floss carrier 22 is an integral part of cap 16 in which case the floss carrier and cap are united by suitable means such as mating threads on the cap 16 and elongated body 13.

In the first embodiment, the insertable portion of floss carrier 22, base surface 20 and peripheral edge 21, may be glued or fixed in some othe fashion in addition to the snug seating discussed above.

Floss carrier 22 also includes a plurality of side walls rising above base surface 20 to a roof surface 25. The side walls, base surface 20 and roof 25 define an enclosed space within which is disposed a significant amount of dental floss preferably wound in some type of compact shape on a spool. As best shown in FIG. 2, end portion 41 of dental floss 32 extends out of a hole or a T-shaped cut-out 43 in side wall 45 of the housing. The bottom extremity 47 of cut-out 43 is proximate base surface 20. The upper bar 49 of cut-out 43 is generally in a plane spaced from but parallel to base surface 20.

On adjacent side wall 51 is attached a cutter plate 26. Cutter plate 26 has, in this embodiment, two tabs 28 and 30 that protrude from the outside surface of side wall 51. Cutting tabs 28 and 30 have cutting edges 53 and 55 that are adopted to cut and separate floss end 41 from the balance of the floss stored within the housing. As clearly shown in FIG. 3, cutting tabs 28 and 30 extend through a plane defined by upper bar portion 49 of cut-out 43. Further, cutting edges 53 and 55 are offset at an acute angle from that plane. This acute angle enables the user to raise floss 32 to the position shown by dashed lines in FIG. 3, pull a predetermined amount of floss from the housing, cut and separate the pulled out portion of floss from the balance of the floss remaining in the housing.

The claims appended hereto are meant to cover modifications and changes within the scope and spirit of the present invention. For example, cutting plate 26 need not be mounted on adjacent side wall 51 with respect to cut-out 43. The side walls do not have to be planar. Various mounting mechanisms can be substituted for the tight-fit mount or screw-type mount. The claims appended hereto are meant to cover these modifications and in general the combination of a dental floss containing portion and a toothpaste containing portion with the latter being of the "pump" type which includes a dispensing orifice and manually maniputable operator means, with a cutter means on the combination so that a length of dental floss threaded through an opening in the floss containing portion may be severed.

What is claimed is:

1. In combination, a dental floss carrying device, a pump-type toothpaste dispenser, and means joining said device and dispenser, said pump-type dispenser comprising:

an elongated body housing toothpaste therein;
   a dispenser mechanism atop said elongated body;
   a top portion removably attached to said elongated body enclosing said dispenser mechanism, said top portion having a peripheral wall extending upward from a top dispenser surface thereby forming a cavity;
   said floss carrying device comprising:
   a base including means for complementary attachment in the cavity to the top of said pump-type toothpaste dispenser;
   a housing attached to said base and defining a substantially enclosed space therebetween, said dental floss being disposed in said enclosed space, said housing having a hole in a side thereof through which extends an end of said dental floss;
   a cutter plate attached to the outside surface of said housing, said cutter plate including a cutting surface protruding out from said outside surface;
   wherein said dental floss is adapted to be pulled from said enclosed space via said hole and after removal of a portion of said dental floss from said enclosed space, said floss portion is adapted to be separated from the remainder of said dental floss by cutting at said cutting surface of said cutter plate; and
   wherein the base of the device includes:
   an insertable portion at the bottom of said base, said insertable portion having a complementary shape as compared to said cavity such that said insertable portion is removably inserted in said cavity to mount the device atop said toothpaste dispenser and said insertable portion defines a substantially, flat surface that is in a parallelly spaced relationship with said top dispenser surface when the device is mounted onto the dispenser.

* * * * *